United States Patent [19]
Potter

[11] Patent Number: 5,219,345
[45] Date of Patent: Jun. 15, 1993

[54] BACKSCATTER MONITORING SYSTEM

[75] Inventor: William R. Potter, Grand Island, N.Y.

[73] Assignee: Health Research, Inc., Buffalo, N.Y.

[21] Appl. No.: 502,183

[22] Filed: Mar. 30, 1990

[51] Int. Cl.⁵ ........................................... A61B 5/0215
[52] U.S. Cl. ....................................... 606/15; 356/39; 356/73.1; 128/633; 128/665; 250/227.11
[58] Field of Search .................. 356/39, 41, 342, 73.1; 250/227.11; 128/633, 634, 632, 665, 655; 606/13, 15

[56] References Cited

U.S. PATENT DOCUMENTS 4,716,288 12/1987 Doi ..................................... 356/73.1
4,795,434 1/1989 Kujawski ............................. 128/634

OTHER PUBLICATIONS

W. B. Beck, Laser Focus (Nov. 1987) 4 pages total.

Primary Examiner—Vincent P. McGraw
Assistant Examiner—La Charles P. Keesee

[57] ABSTRACT

A system for monitoring the condition of the distal tip of an optical treatment fiber, including a monitor for measuring the intensity of light backscattered from the distal tip. A treatment laser is coupled to a jumper fiber, which has its distal end optically coupled to the proximal end of the treatment fiber, for transmitting light from the laser to treatment tissue at a treatment site in a patient. The monitor determines the amount of laser light backscattered from the distal tip of the treatment fiber, thereby indicating whether an abnormal condition exists at the distal tip. At least one additional fiber is optically coupled to the treatment fiber for receiving tip backscatter unpolluted by interface backscatter between the jumper fiber and the treatment fiber. Additional fibers may also be optically coupled to the treatment fiber for receiving and monitoring the tip backscatter light or return light from the treatment tissue.

5 Claims, 4 Drawing Sheets

FLUORESCENCE DETECTOR AND TUNED AMPLIFIERS

BACKSCATTER MONITORING SYSTEM

This invention was made wholly or partially under a grant from The National Institute of Health number CA16717. The United States Government may have certain rights in this invention.

BACKGROUND OF THE INVENTION

This invention relates to a method and apparatus for monitoring the conditions on and in the neighborhood of the distal end of a fiber optic within the body of a patient being treated with light (usually from a laser) delivered through this fiber optic, for ablating or otherwise treating tissue at a treatment site within the patient.

In conventional methods for monitoring such conditions, laser light is transmitted from a laser to the treatment site via a first fiber optic, known as a jumper, and a second fiber optic, which may be referred to as a treatment fiber and which has its proximal end optically coupled to the jumper and its distal end positioned at the treatment site within the patient. Typically, the jumper is smaller in diameter than the treatment fiber.

In such treatment, light is scattered (such as by fluorescence) from tissue at the treatment site, and is monitored for determining the status of tissue at the site. An example of such treatment is described in applicants' U.S. Pat. No. 5,111,821 issued May 12, 1992 entitled "In Vivo Fluorescence Photometer," by William R. Potter, which is incorporated herein by reference. The light which is scattered by the tissue at the treatment site may be monitored by using a directional tap on the jumper.

Fiber optic delivery systems of conventional design which are used in clinical photodynamic therapy (PDT) utilize a long (10-30 meter), 100 um-core quartz fiber (i.e., the jumper) which conducts light from a dye laser to the treatment room in a hospital. The distal end of the jumper (i.e., the end farther from the laser) is held against the proximal end of a 400 um core treatment fiber, utilizing conventional SMA-type connectors and other hardware as necessary. Light is thus transferred to the treatment fiber.

The treatment fiber is usually about 2 meters long, and its distal tip is modified to provide the required light distribution. Light may be required to escape in a uniform fashion along a prescribed length (typically 0.5 to 4.0 cm), thus forming a cylindrical light source. Alternatively, the treatment may require a source with spherical symmetry ( a "light bulb"), or the fiber may be tipped with a short focal length lens (e.g., 1-3 mm) which projects an image of the fiber tip. Treatment is frequently done through an endoscope.

A drawback to systems presently in use is that continuous monitoring of the fiber tip once it is in the patient has not yet been possible. The usual monitoring technique has been to measure the light leakage from the 100 um core jumper. However, this ensures only that the power in the fiber remains constant, and is not very sensitive to failure of the tip.

It is possible for blood or tissue to carbonize the tip, with a concomitant decrease in the amount of treatment laser light reaching the tumor. Because the eye is not an accurate device for fine discrimination of light levels, a method and apparatus for monitoring the tip of the treatment fiber are needed. Such a method and apparatus are also needed which allow inspection of the fiber tip during actual treatment, which is not possible with conventional designs, because the tip is often embedded in tumor during treatment.

SUMMARY OF THE INVENTION

It is therefore an object of the invention to provide a method and apparatus for monitoring light which is backscattered from the distal tip of a treatment fiber. The invention includes a large-diameter treatment fiber and smaller-diameter jumper as described above, with a conventional laser treatment system being coupled to the jumper at its proximal end.

The present system monitors the light which is backscattered at the interface between the distal tip of the treatment fiber and the patient's tissue, because of the different indexes of refraction of these two media. This gives an indication of the amount of carbonization at the distal tip of the treatment laser, because the amount of backscatter light varies with the amount of carbonization.

In one embodiment of the invention, the light which is backscattered from the distal end of the treatment fiber may be monitored by detecting it after it has traveled back up the treatment fiber and back through the jumper.

In a preferred embodiment of the invention, one or more additional fibers are positioned adjacent the jumper, and are also optically coupled to the treatment fiber. However, these additional fibers are not coupled to the laser, and are used only for detecting return light from the treatment site. The additional fibers thus detect backscatter light from the distal end of the treatment fiber, and also detect light scattered from the tissue under treatment; but they do not detect any light which may be reflected at the interface between the jumper and the treatment fiber. Thus, this embodiment of the invention provides for measurement of the backscatter light relatively independently of contamination by reflections within the laser light delivery system.

Other features of the invention are described more fully in the following discussion.

DESCRIPTION OF THE PREFERRED EMBODIMENTS

The system of the present invention is utilized to measure the amount of backscattered light from the distal tip of an optical fiber. The system is useful for many different optical fiber applications, but will be described herein in the preferred embodiment of measuring the backscatter from the distal tip of the fiber utilized in laser surgery.

Figures 1, 2:
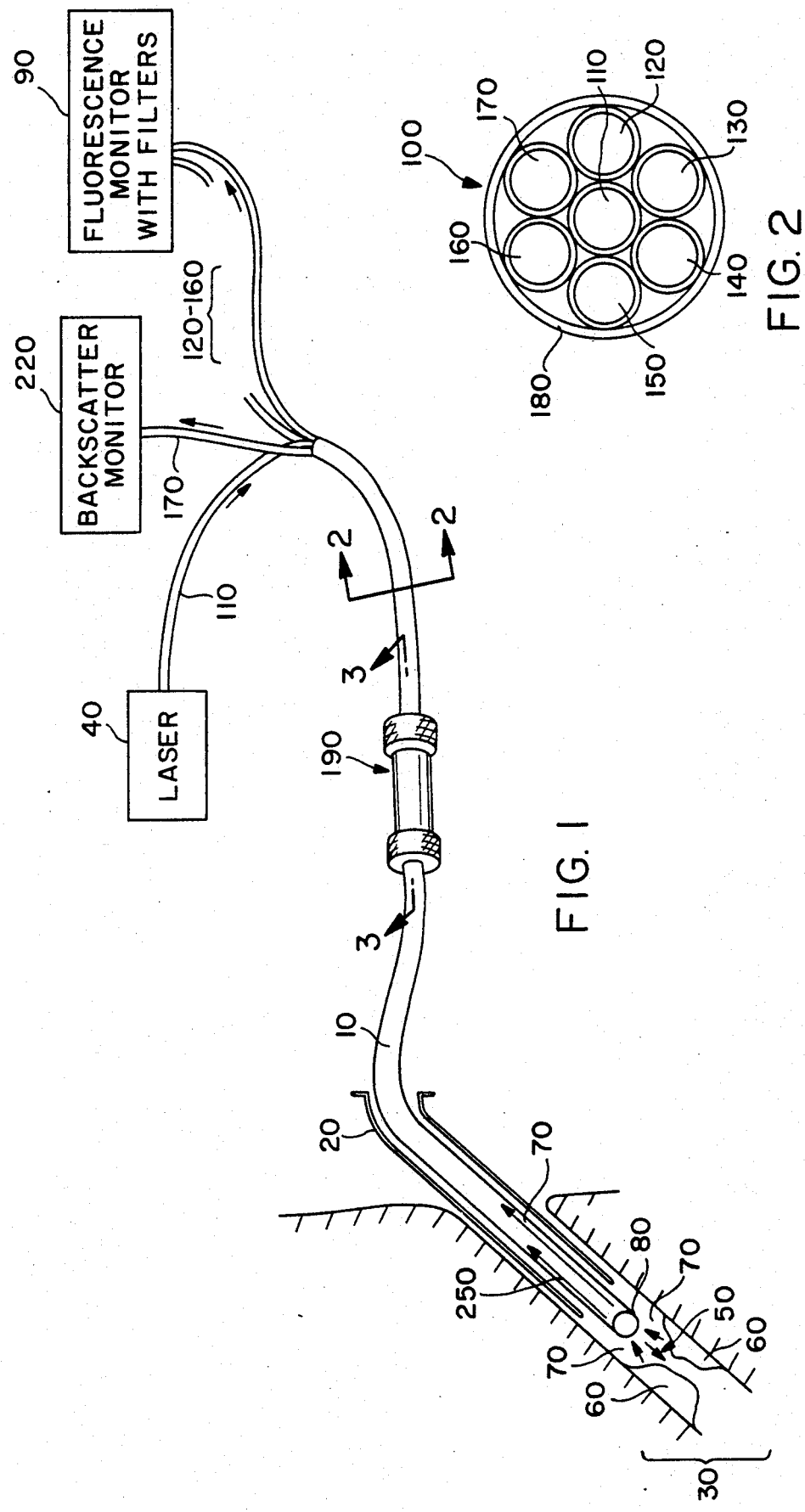
FIG. 1 is a diagram of apparatus according to the present invention.
FIG. 2 is a sectional view taken along line 2—2 of FIG. 1.
Figures 5, 6:
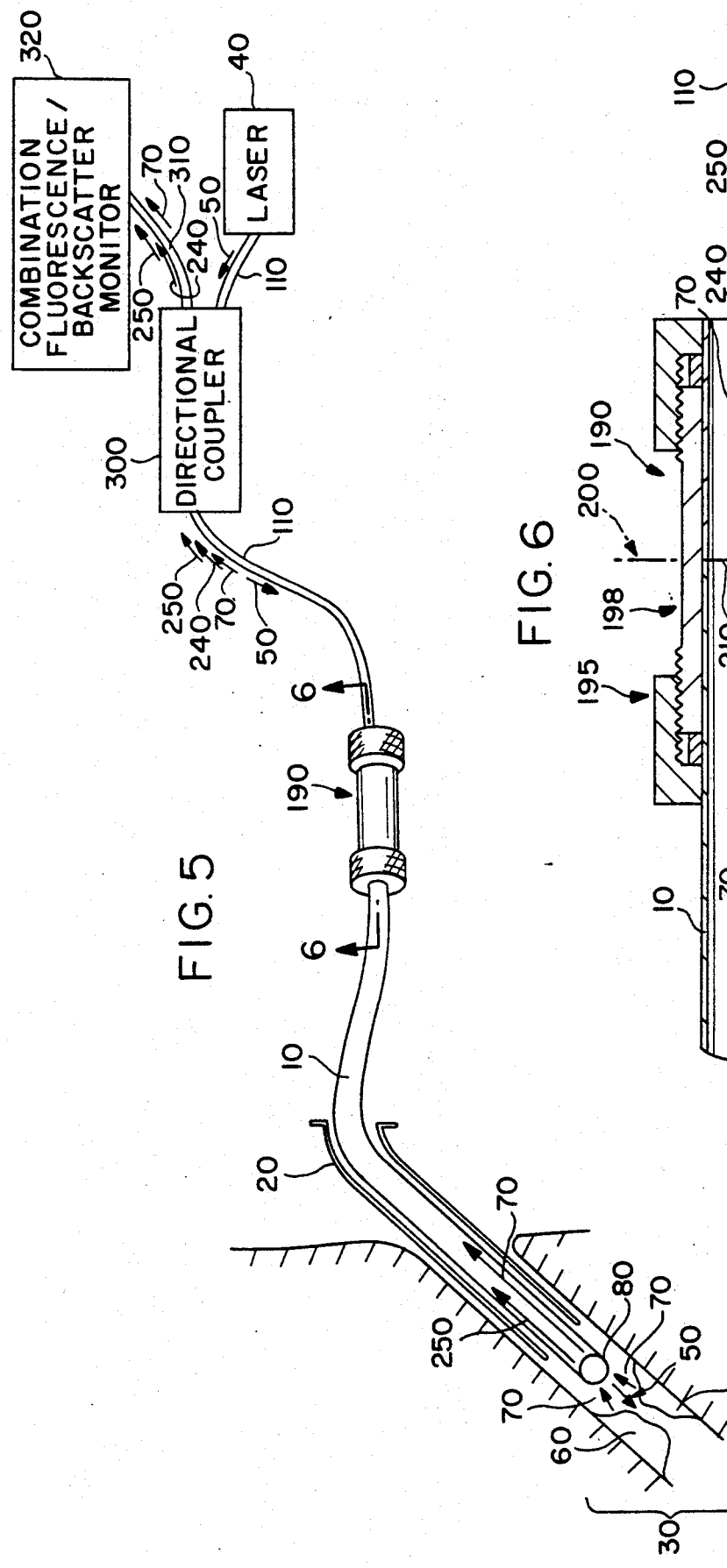
FIG. 5 shows an alternative embodiment of the apparatus of FIG. 1.
FIG. 6 is a sectional view taken along the line 6—6 of FIG. 5.

In laser surgery, an optical fiber 10, as shown in the embodiments of FIGS. 1 and 5, is inserted via a catheter 20 or other means into a vessel 30 of a patient. A laser 40 has an output which is optically coupled (via a fiber 110) to the fiber 10, which transmits laser light 50 to treatment tissue 60 (which may be plaque or other occlusions) within the vessel 30. Return light 70, which may be due to fluorescence, reflection, or the like, returns from the tissue 60 back into a distal tip 80 of the optical fiber 10. This return light travels up the optical fiber 10 and the fiber 110, ultimately reaching a fluorescence monitor 90 (in FIG. 1) or a combination backscatter/fluorescence monitor 320 (in FIG. 5).

The fibers 10 and 110 are preferably quartz fibers, with their ends being polished to a low scattering finish in a conventional manner, using abrasive coated plastic sheets of progressively finer grit. The fibers are preferably clad with a thin (10–20 um) layer of hard transparent polymer. This cladding is of lower refractive index than the core. It is also possible to use graded index fiber of all-quartz construction. These designs are standard in fiber optic technology.

The monitors 90 and 320 are used to monitor the status of the plaque, tumor or other tissue 60, and are discussed in further detail below. The fluorescence monitoring may be carried out as described, for instance, in the above-mentioned U.S. Pat. No. 5,111,821 issued May, 12, 1992. The tissue fluorescence may be due to tumor, to plaque-localizing drugs, or to endogenous plaque or tumor fluorescence. It is best characterized by the use of interference filters or, if sufficiently strong, by the less efficient grating or prism monochrometers. A quite flexible and sensitive device for fluorescence analysis is the rotating variable wavelength interference filter. Such a filter can be used efficiently with fibers through the use of two small lenses of approximately 12 mm diameter. A readout device (not separately shown) may be used with the monitor 90 or the monitor 320, such as a digital voltmeter, chart recorder, and/or a voltage-to-frequency converter.

In the embodiment of FIG. 5, the fiber 110 is held in place relative to the fiber 10 by means of conventional SMA connectors 190 and 195, forming an interface 230 between the distal end of the fiber 110 and a proximal face 210 of the fiber 10, as shown in FIG. 6. The interface 230 lies on an interface plane 200. The optical output element (not separately shown) of the laser (or lamp) is likewise coupled in a fixed fashion to the fiber 110.

The SMA connectors 190 and 195 are held together with a threaded bushing 198 designed for this purpose. In this configuration, both SMA connectors 190 and 195 are identical devices used in conjunction with the fiber 110 and available from Augat Fiber Optics and other sources. The attachment is secured by epoxy or crimping, or a combination of epoxy and crimping. Other conventional means for maintaining the fibers in a fixed end-to-end configuration may be used.

As laser light 50 travels down the fiber 110, and traverses the interface plane 200 at interface 230, a certain amount of interface backscatter light is reflected back up the fiber 110 due to the optical interface 230. Another reflection takes place as the light 50 enters the fiber 10. Together, these constitute interface backscatter light 240.

A similar effect occurs as the laser light 50 passes the distal tip 80 of the fiber 10. That is, there is another interface reflection at the distal tip 80, resulting in tip backscatter light 250 returning up the fiber 10 and the fiber 110.

Finally, return light 70 also travels up the fiber 10 and the fiber 110, such that the light which returns to the proximal end of the fiber 110 includes backscattered light both from the interface 230 and from the distal tip 80 (i.e., light 240 and 250) and return light 70 from the patient's tissue.

The return light 70 is used in monitor 320 to determine the status of the treatment tissue of the patient. Since the return light 70 is typically of a different wavelength than the incident treatment light 50 and the reflected light 240 and 250, it is possible to differentiate, by the use of conventional filters (not separately shown) between the return light 70 and the backscatter light 240 and 250. The intensity measurement is carried out in any conventional manner, such as by using a photodiode power meter.

Figure 7:
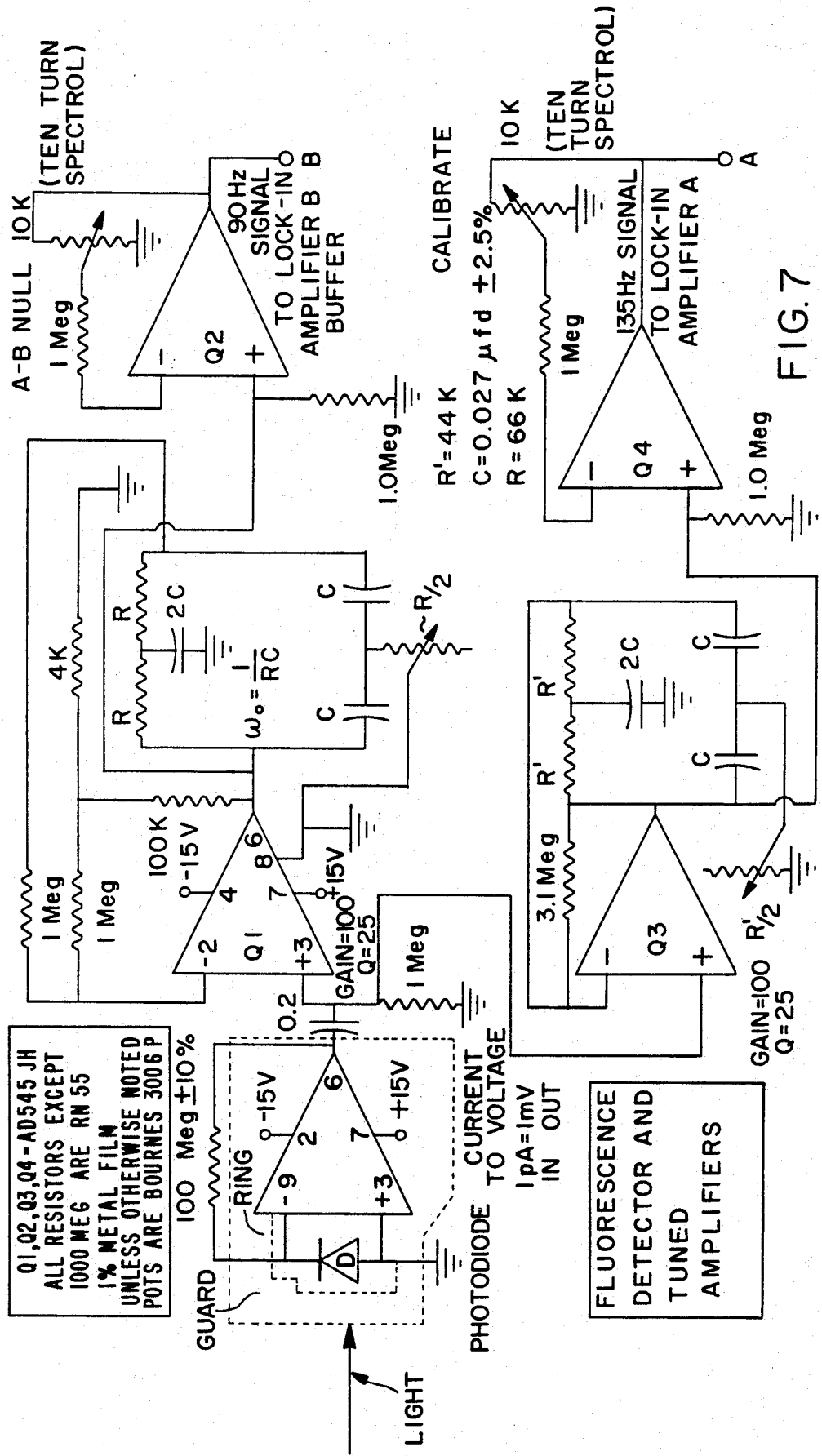
FIG. 7 is a schematic diagram of a photodetecting circuit for use with the invention.

For instance, the intensity of either the return light 70 or the backscatter light may be measured by the circuit shown in FIG. 7, which is fully described relative to FIG. 2 of the above-mentioned copending U.S. Pat. No. 5,111,821 issued May 12, 1992. The only differences between the schematic of FIG. 7 herein and FIG. 2 of the copending application are that in FIG. 7, a 10-to-100 megohm resistor may be used instead of a 1000 megohm resistor, and the 690 nm filter is omitted from FIG. 7. In general, the value of the resistor is chosen the intensity of the backscatter signal, to adjust the sensitivity of the circuit.

It is important to know the condition of the tip 80 while laser treatment of the patient proceeds. If carbonization occurs at the tip 80, this will reduce the amount of the treatment laser light 50 reaching the treatment tissue 60. Thus, by monitoring the condition of the tip 80, the operator of the system can determine whether the treatment light 50 is efficiently reaching the treatment tissue 60.

The condition of the tip 80 may be monitored by determining at any given time the amount of tip backscatter light 250 therefrom. This is because carbonization of the distal tip 80, in addition to reducing the amount of transmitted laser light, also affects the amount of tip backscatter (in most cases, reducing the amount of backscatter). The present invention is therefore designed to inspect the tip backscatter light 250 by constantly monitoring its intensity.

It is also possible that a portion of the treatment light 50 will be reflected from the treatment tissue 60 back through the tip 80 and up the fiber 10. If this occurs, the reflected light will be the same wavelength as the tip backscatter light 250, and will be therefore indistinguishable from it. Thus, reflection from the tissue will increase the amount of apparent tip backscatter. This does not present a problem in the detection of carbonization or other phenomena which decrease the amount of tip backscatter, since the tissue reflectance is also reduced by tip carbonization. Moreover, the detection of an increase is itself useful, because it may indicate an unwanted movement of the distal tip 80 or undesirable proximity to tissue.

In the embodiment of FIG. 5, the total intensity of the backscatter light 240 and 250 returning to the proximal end of the fiber 110 is detected. This can be done by using a conventional directional coupler 300 and a fiber leakage monitor (not separately shown) in conjunction with the fiber 110. The leakage monitor, which detects leakage into the cladding of an optical fiber and may be of the design discussed in U.S. Pat. No. 4,889,129 should be placed far enough from the tip 80 to avoid spurious signals from the tip. The directional coupler 300 may be of conventional design, such as the system described in the article "Tapping Optical Fibers," by William B. Beck, *Laser Focus*, November 1987, which is incorporated herein by reference.

The aggregate backscatter light 240 and 250 and return light 70 is tapped off by the coupler 300, and is shunted via an optical fiber 310 to the combination fluorescence/backscatter monitor 320. The monitor may 320 include filters, as mentioned above, for differentiating between the return light 70 and the backscatter light 240 and 250. Thus, the intensity of the backscatter light may be determined independently of the intensity of the return light.

Given a constant intensity of the treatment light 50, and given a constant interface backscatter 240 from the interface 230, any variation in the intensity of the aggregate of the backscatter light 240 and 250 must be due to changes in the amount of backscatter light 250 from the tip 80. Since carbonization generally reduces the backscatter from the tip 80, a reduction of backscatter intensity will indicate some degree of carbonization. Other effects (including increased backscatter from the tip 80, as indicated above) may occur, and may be empirically correlated to abnormal or undesirable conditions of the proximal tip 80.

In use, the monitor 320 is set to monitor the intensity of the total backscatter light 240 and 250, and includes means for storing or recording the intensity as a function of time, in addition to displaying the intensity so that the operator of the system can determine at any time the condition of the distal tip 80. An alarm (such as a buzzer or a flashing light) is preferably set to trigger when the reading fluctuates by more than a preset window, such as 10%. In general, the operator may select an intensity value in advance, by determining empirically in advance an acceptable backscatter intensity, and then set the alarm or other indicator to flag when the intensity has deviated by more than a predetermined amount from the selected value. This may be accomplished with standard circuits. With this system, the operator may then proceed with the laser surgery or other operation, and will be automatically notified when the distal tip is carbonized or otherwise compromised.

Figure 3:
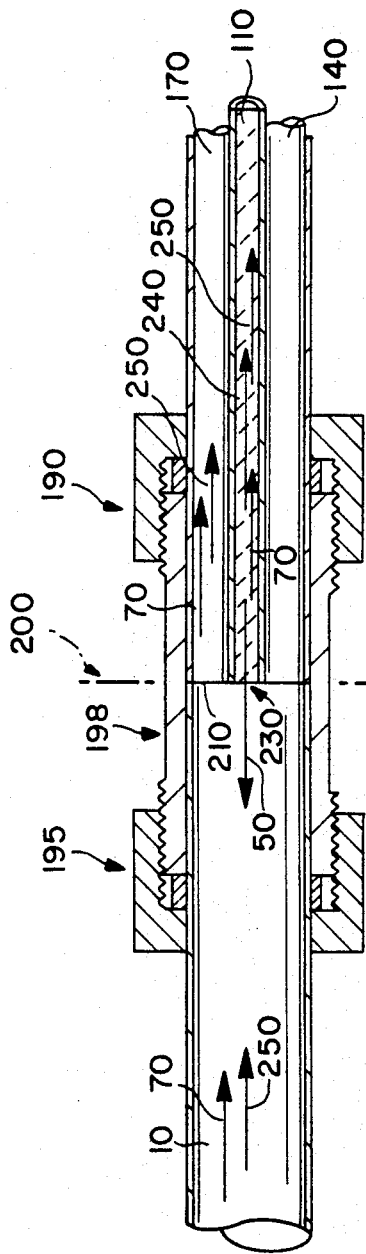
FIG. 3 is a sectional view taken along line 3—3 of FIG. 1.

In the embodiment of FIG. 5, the intensity of the interface backscatter 240 may be so great as to mask the monitored intensity of the tip backscatter 250, depending on the characteristics of the equipment chosen for the system, such as the stability of the output from the laser 40 and the dimensions and quality of the fibers 110 and 10. Therefore, while the embodiment of FIG. 5 measures the total backscatter 240 and 250 to determine the condition of the tip 80, the embodiment of FIGS. 1-3 is designed to eliminate the interface backscatter 240 from being detected at the backscatter monitor.

The exclusion of the backscatter light 240 can be very significant. In a typical laser treatment system, the jumper fiber 110 may be 100 microns in diameter, while the treatment fiber 10 may be 400 microns in diameter. In such a system, the ratio of the area of the fiber 110 to the area of the fiber 10 is 1:16. Since the return light 70 typically is evenly distributed across the interface 200, the fiber 110 shown in FIG. 5 therefore receives only 1/16 of the total amount of return light 70 and tip backscatter light 250. However, since the treatment light 50 is transmitted through the fiber 110, the fiber 110 receives the entire amount of backscatter light 240 due to reflections at the interface 230.

The relative intensities of the interface backscatter light 240 and tip backscatter light 250 may be estimated as follows. In typical settings, the backscatter at each optical fiber interface is approximately 4%. Thus, there is a 4% reflection as the laser light 50 leaves the fiber 110, and an additional 4% reflection as the light 50 enters the fiber 10. The laser light 50 that enters the fiber 10 is therefore only approximately 92% of its original intensity, and the interface backscatter 240 amounts to about 8% of the original intensity of the light 50.

The tip backscatter from the tip 80 also amounts to approximately 4% of the incident treatment light on the tip. Since only 1/16 of this tip backscatter light is received into the fiber 110 (given the dimensions discussed above), the ratio of the amount of tip backscatter 250 to the amount of backscatter light 240 traveling back up the fiber 110 is as follows:

$$\frac{\text{(Collected Tip Backscatter)}}{\text{(Total Interface Backscatter)}} = \frac{0.04 \times 1/16}{0.08} = 1/32$$

Thus, the intensity of the backscatter light 240 in the fiber 110 is approximately 32 times that of the tip backscatter light 250. As a result, fluctuations in the interface backscatter light 240 may totally mask fluctuations in the tip backscatter light 250. For instance, since power output of lasers is generally not constant, a very small fluctuation in the power output of the treatment laser 40 may result in a fluctuation of the interface backscatter light 240 which is far greater than the amount of tip backscatter light 250 being monitored. In the above example, a variation of as little as 3% (i.e., 1/32) of the total intensity of the treatment laser light 50 will result in the light 240 entirely masking the tip backscatter light 250.

With lower cost lasers having unpredictable output characteristics, it is therefore preferable to utilize the configuration of FIGS. 1-3, wherein in features of the system which are similar to those of FIGS. 5-6 are numbered the same. In this embodiment, an optical fiber cable 100 is utilized. The cable 100 includes the core jumper fiber 110, and (as shown in FIG. 2) six circumferentially positioned fibers 120, 130, 140, 150, 160 and 170. These may be identical conventional optical fibers, including cladding layers, as shown in FIG. 2, and surrounded by a sheath 180. Thus, in the system of FIGS. 1-3, a 1×7 fiber optic cable is formed, although other numbers of circumferential fibers may be used.

The fibers 110-180 of the 1×7 cable 100 are optically coupled to the fiber 10 by means of the conventional SMA connectors 190 and 195, as shown in FIG. 3. The interface plane 200 is the plane at which each of the fibers 110-170 abuts the proximal face 210 of the fiber 10. As shown in FIG. 1, at least one of the fibers 110-170 is coupled to a backscatter monitor 220. In the preferred embodiment, a single fiber, such as optical fiber 170, is coupled to the monitor 220.

The fibers 120-170 receive a portion of the return light 70 traveling from the distal tip 80. Because the fibers 110-170 are not utilized for transmitting the treatment laser light, they are optically isolated from the coupling between the fibers 10 and 110 at the interface 230. Therefore, there is no contribution of backscatter from the backscatter light 240 arising at the interface plane 200.

In the embodiment of FIGS. 1-3, the fibers 110-170 are each 100 um in diameter, and the treatment fiber 10 is 400 um in diameter. Other diameters are possible, though in general the total diameter of two of the fibers 120-170 plus the diameter of the jumper fiber 10 should not exceed the diameter of the treatment fiber 10. The jumper fiber may, for example, be 200 um in diameter, in which case the total diameters of the circumferential fibers, including cladding layers, should not exceed 200 um, or 100 um each. Alternatively, the fibers 110-170 may all be 133 um in diameter, which maximizes the amount of return light 70 and tip backscatter 250 which is received from the fiber 10.

One or more of the fibers 120-170 may be used to transmit the return light 70 to the backscatter monitor 220. In the embodiment of FIG. 1, only the fiber 170 is coupled to the backscatter monitor 220. Although the return light 70 also travels up the fiber 170, it is preferably filtered out or otherwise excluded from the measurement of the intensity of the return light 250. The fibers 120-160 transmit the return light 70 to the fluorescence monitor 90, which is used to determine the status of the tissue 60 as discussed above.

Thus, in this system, the tip backscatter light 250 travels up the fiber 170 unpolluted by the interface backscatter light 240. Monitoring the intensity of the light 250 via the fiber 170 therefore yields a reliable status report on the condition of the tip 80. In particular, variations in the power output of the laser 40 will have a greatly reduced effect in this system compared with the embodiment of FIG. 5. For example, a 5% variation in the intensity of the treatment light 50 will result in only a concomitant 5% variation in the intensity of the tip backscatter 250. Since the interface backscatter 240 is excluded, the 5% variation will not appear as a large change masking the tip backscatter signal.

Another advantage of the embodiment of FIG. 1-3 is that it eliminates inaccuracies which may arise from the use of the directional coupler 300 and the leakage monitor of FIG. 5, which are subject to inconsistencies due to spurious influences, such as flexing of the fiber 110.

Any one or more of the six fibers 120-170 provides an adequate signal for either backscatter or fibers (such as 160 and 170) might be used in two different backscatter monitors, for instance if a dual-wavelength laser treatment system is used. Likewise, different fibers of the fibers 120-170 may be coupled to different fluorescence monitors or other such devices for detecting the status of the treatment tissue.

Figure 4:
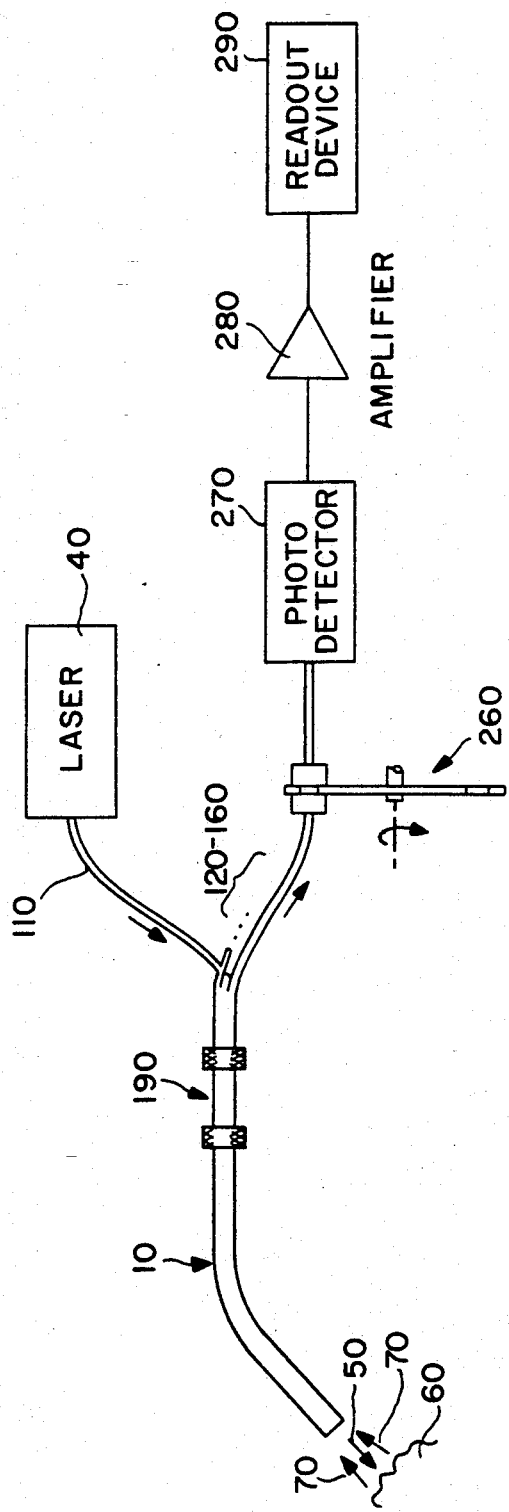
FIG. 4 shows an alternative embodiment of the proximal end of the treatment system shown in FIG. 1.

In the embodiment of FIG. 4, the fibers 120-160 shown in FIG. 1 are coupled to the fluorescence monitor 90, which is provided with filters on a filter wheel 260, or other means for selecting specific wavelengths for inspection. Once passing through the appropriate filter from the filter wheel 260, the return light is sent to a photodetector 270, and is then amplified by amplifier 280, and is displayed or stored via a readout device 290. These steps are conventional in the art.

What is claimed is:

1. An optical fiber system for treating a patient with light while monitoring a treatment fiber, comprising:
    a first "treatment" optical fiber having a proximal end at which treatment light is received and a distal end at which the received light is emitted onto a patient;
    a second optical fiber for transmitting treatment light onto the proximal end of the fist optical fiber, the second optical fiber having a first end aligned end to end with the proximal end of the first optical fiber;
    a third optical fiber for receiving a portion of light which travels via the distal end of the first optical fiber back to the proximal end of the first optical fiber, the third optical fiber having a first end aligned end to end with the proximal end of the first optical fiber, the third optical fiber optically isolated from the second optical fiber;
    a light monitor coupled to the third optical fiber for detecting the back traveling portion, the monitor including means for measuring an intensity of the portion; and
    means for generating an output related to said measured intensity; and
    wherein the first end of both the second optical fiber and the third optical fiber fit within a circumference of the proximal end of the first optical fiber.

2. The system of claim 1 further comprising means for aligning the first ends of the second and third optical fibers with the proximal end of the first optical fiber.

3. The system of claim 1 wherein the light monitor is for monitoring backscatter from the distal tip of the first optical fiber.

4. The system of claim 1 wherein the light monitor is for monitoring fluorescence reflected back into the distal tip of the first optical fiber.

5. The system of claim 1 wherein the light monitor is a first light monitor for monitoring backscatter from the distal tip of the first optical fiber, and further comprising:
    a fourth optical fiber for receiving a portion of light which travels via the distal end of the first optical fiber back to the proximal end of the first optical fiber, the fourth optical fiber having a first end aligned end to end with the first optical fiber, the fourth optical fiber optically isolated from the second optical fiber; and
    a second light monitor coupled to the fourth optical fiber for detecting "fluorescence" light returning into the distal tip of the first optical fiber.

* * * * *